United States Patent
Jain et al.

(10) Patent No.: US 8,067,619 B2
(45) Date of Patent: *Nov. 29, 2011

(54) COUMARIN DERIVATIVES AS ION CHANNEL OPENERS

(75) Inventors: Nareshkumar F. Jain, Exton, PA (US); Zhihua Sui, Exton, PA (US)

(73) Assignee: Janssen Pharmaceutica N.V., Beerse (BE)

( * ) Notice: Subject to any disclaimer, the term of this patent is extended or adjusted under 35 U.S.C. 154(b) by 2 days.

This patent is subject to a terminal disclaimer.

(21) Appl. No.: 12/624,686

(22) Filed: Nov. 24, 2009

(65) Prior Publication Data

US 2010/0069474 A1    Mar. 18, 2010

Related U.S. Application Data

(62) Division of application No. 11/334,679, filed on Jan. 18, 2006, now Pat. No. 7,662,975.

(60) Provisional application No. 60/645,702, filed on Jan. 21, 2005.

(51) Int. Cl.
*C07D 311/00* (2006.01)
*C07D 311/02* (2006.01)

(52) U.S. Cl. ....................... 549/283; 549/290

(58) Field of Classification Search .................. 549/290, 549/283

See application file for complete search history.

(56) References Cited

U.S. PATENT DOCUMENTS

| | | | |
|---|---|---|---|
| 4,749,798 A | 6/1988 | Gandolfi et al. | |
| 4,845,242 A | 7/1989 | Powers et al. | |
| 6,331,562 B1 | 12/2001 | Bhagwat et al. | |
| 2005/0080082 A1 | 4/2005 | Hewawasam et al. | |

FOREIGN PATENT DOCUMENTS

| WO | WO 03/043977 A1 | 5/2003 |
|---|---|---|
| WO | WO 2004/035002 A2 | 4/2004 |

OTHER PUBLICATIONS

Edwards, G. et al.: "Structure—activity relationships of K+channel openers"; TiPS, Oct. (1990) 11: 417-422.
Sato, H. et al.: "Vasorelaxant Activity of 2-fluoroalkyl-6-nitro-*2H*-1-Benzopyran-4-carbothioamide and—carboxamide K+Channel Openers"; Bioorganic & Med. Chem. Ltrs. (1995) 5(3): 233-236.
Taka, N. et al.: "6-Substituted 2,2-Bis(fluoromethyl)-benzopyran-4-carboxamide K+Channel Openers"; Bioorganic & Med. Chemistry (2000) 8: 1393-1405.
Database Beilstein, Beilstein Institut zur Furderung der Wissenschaften, Frankfurt/Main, DE; XP002392763; J. Indian Chem. Soc., vol. 21 (1994) p. 44.
Database CA [Online] Chemical Abstracts Service Columbus, Ohio, US; Thakar, K.A.: "Condensation of m-halophenols with acetonedicarboxylic acid in presence of sulfuric acid"; XP002392764; J. Indian Chem. Soc. (1963), 40(5), p. 397.
Database Chemcats [Online], Chemical Abstracts Serivce, Columbus, Ohio, US; XP002392765; Enamine Screening Library, Jan. 24, 2006. Abstract.
PCT International Search Report relating to International Patent Application No. PCT/2006/001927; date of mailing Aug. 10, 2006.
PCT Written Opinion for International Application No. PCT/2006/001927.

*Primary Examiner* — Andrew D. Kosar
*Assistant Examiner* — Raymond Covington
(74) *Attorney, Agent, or Firm* — Jeremy K. McKown

(57) ABSTRACT

The present invention is directed to coumarin derivatives, pharmaceutical compositions containing them and their use in the treatment of disorders related to ion channels such as potassium channels.

7 Claims, No Drawings

COUMARIN DERIVATIVES AS ION CHANNEL OPENERS

CROSS REFERENCE TO RELATED APPLICATIONS

This Application is a divisional application of U.S. application Ser. No. 11/334,679, filed Jan. 18, 2006 now U.S. Pat. No. 7,662,975, which claims priority to U.S. Provisional Patent Application No. 60/645,702, filed Jan. 21, 2005, the disclosures of which are hereby incorporated by reference in their entireties.

FIELD OF THE INVENTION

The present invention is directed to novel coumarin derivatives, pharmaceutical compositions containing them and their use in the treatment of disorders related to ion channels such as potassium channels. The compounds of the invention are thus useful for the treatment of various disorders. This includes but is not limited to urinary incontinence, overactive bladder, hypertension, erectile dysfunction, female sexual disorders, dysmenorrhea, irritable bowl syndrome, airway hyperactivity, epilepsy, stroke, Alzheimer's and Parkinson's diseases, myocardial injury, coronary artery disease as well as hair loss and baldness.

BACKGROUND OF THE INVENTION

Ion channels play a fundamental role in the homeostasis of cell function through the regulation of the transmembrane movement of ions. Cellular activity can be affected by modifications of the activities of the ion channels. This leads to changes in membrane potential difference. Potassium channels are a diverse and ubiquitous group of ion channels. They principally regulate the resting membrane potential of the cell and attenuate the level of excitation of cells. A functional $K_{ATP}$ channel is a hetero-octamer assembled from four inward rectifying potassium channel subunits (Kir6.2) and four sulfonylurea receptor (SUR) subunits. There are two SUR genes, SUR1 and SUR2. SUR1/Kir6.2 channels are found in the pancreas and brain. Two major splice variants arise from the SUR2 gene, SUR2A and SUR2B, that differ only at the C-terminal 42 amino acids. SUR2A/Kir6.2 channels are found in cardiac and skeletal tissues whereas SUR2B/Kir6.2 channels are found in smooth muscles of many tissues including bladder (Aguilar-Bryan, 1998). A number of diseases or conditions may be treated with potassium channel openers. This includes overactive bladder, urinary incontinence, male erectile dysfunction, female sexual disorders, premature labor, benign prostate hyperplasia (BPH), dysmenorrhea, neurodegeneration, stroke, pain, coronary artery disease, angina, ischemia, eating disorders, irritable bowl syndrome and alopecia.

Urinary incontinence (UI) is a disease that can affect the overall quality of life of a patient. Overactive bladder (OAB) is the most prevalent form of UI, with reported prevalence rate from 40 to 70% of all diagnosed UI cases (Wein, 2000). OAB is characterized by the symptoms of increased urinary frequency, urgency, and involuntary loss of urine. A primary cause of OAB is an oversensitive bladder that contracts unexpectedly and involuntarily. The ideal pharmaceutical agent should suppress the involuntary contraction while leaving the normal voiding contractions intact. ATP-sensitive potassium channel openers (KCO) could serve as such agents. The ATP-sensitive potassium channels ($K_{ATP}$) are expressed in bladder smooth muscle and function as key regulators of the resting membrane potential in these cells. Compounds that selectively open these channels hyperpolarize the cell and decrease cellular excitability, resulting in suppression of involuntary bladder contractions, while leaving the normal micturition circuitry intact.

SUMMARY OF THE INVENTION

The present invention is directed to a compound of formula (I)

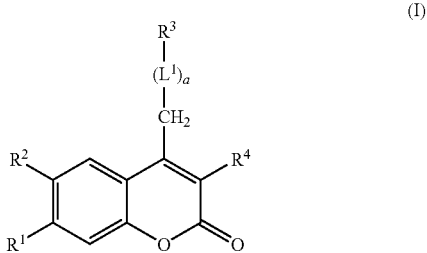

wherein $R^1$ is selected from the group consisting of hydrogen, halogen, cyano, nitro, $CF_3$ and —O—$SO_2$—$CF_3$;

$R^2$ is selected from the group consisting of hydrogen, halogen, cyano, nitro, $CF_3$ and —O—$SO_2$—$CF_3$;

provided that $R^1$ and $R^2$ are not each hydrogen;

a is an integer from 0 to 1;

$L^1$ is selected from the group consisting of —C(O)—, —CH(OH)— and —C(O)—$NR^A$—; wherein $R^A$ is selected from hydrogen or $C_{1-4}$alkyl;

$R^3$ is selected from the group consisting of hydrogen, $C_{1-4}$alkyl, $C_2$alkenyl, aryl and heteroaryl; wherein the aryl or heteroaryl is optionally substituted with one or more substituents independently selected from halogen, hydroxy, $C_{1-4}$alkyl, $C_{1-4}$alkoxy, cyano, nitro or $CF_3$;

alternatively, -$L^1$-$R^3$ is selected from -MOM or -SEM;

provided that when a is 0 ($L^1$ is absent), then $R^3$ is other than hydrogen or $C_{1-4}$alkyl;

provided further that when a is 1 and $L^1$ is —CH(OH)—, then $R^3$ is other than hydrogen;

$R^4$ is selected from the group consisting of hydrogen, aryl, —C(O)-aryl, 6-membered heteroaryl and —C(O)-(6 membered heteroaryl); wherein the aryl or heteroaryl group, whether alone or as part of a substituent group is optionally substituted with one or more substituents independently selected from halogen, hydroxy, $C_{1-4}$alkyl, $C_{1-4}$alkoxy, cyano, nitro or $CF_3$;

provided that when $R^1$ is hydrogen or halogen, $R^2$ is hydrogen, a is 0 ($L^1$ is absent) and $R^3$ is 4-hydroxy-phenyl, then $R^4$ is other than 4-chlorophenyl;

provided further that when $R^1$ is halogen, $R^2$ is hydrogen, a is 1, $L^1$ is —C(O)NH— and $R^3$ is phenyl, then $R^4$ is other than hydrogen;

or a pharmaceutically acceptable salt thereof.

The present invention is further directed to 3-(4-chlorobenzoyl)-4-methyl-2-oxo-2H-chromene-7-carbonitrile and pharmaceutically acceptable salts thereof.

Illustrative of the invention is a pharmaceutical composition comprising a pharmaceutically acceptable carrier and any of the compounds described above. An illustration of the invention is a pharmaceutical composition made by mixing any of the compounds described above and a pharmaceutically acceptable carrier. Illustrating the invention is a process for making a pharmaceutical composition comprising mixing any of the compounds described above and a pharmaceutically acceptable carrier.

Exemplifying the invention are methods of treating disorders related to ion channels, preferably potassium ion channels, more preferably ATP-sensitive potassium ion channels, in a subject in need thereof comprising administering to the subject a therapeutically effective amount of any of the compounds or pharmaceutical compositions described above.

An example of the invention is a method for treating a disorder selected from the group consisting of urinary incontinence, overactive bladder, hypertension, erectile dysfunction, female sexual disorders, dysmenorrheal, irritable bowl syndrome, airway hyperactivity, epilepsy, stroke, Alzheimer's and Parkinson's diseases, myocardial injury, coronary artery disease, hair loss and baldness, in a subject in need thereof comprising administering to the subject an effective amount of any of the compounds or pharmaceutical compositions described above.

Another example of the invention is the use of any of the compounds described herein in the preparation of a medicament for treating: (a) urinary incontinence, (b) overactive bladder, (c) hypertension, (d) erectile dysfunction, (e) female sexual disorders, (f) dysmenorrhea, (g) irritable bowl syndrome, (h) airway hyperactivity, (i) epilepsy, (j) stroke, (k) Alzheimer's disease, (l) Parkinson's disease, (m) myocardial injury, (n) coronary artery disease, (o) hair loss or (p) baldness, in a subject in need thereof.

DETAILED DESCRIPTION OF THE INVENTION

The present invention is directed to compounds of formula (I)

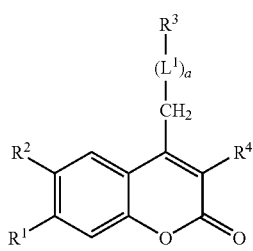

wherein $R^1$, $R^2$, $R^3$, $R^4$, a and $L^1$ are as herein defined. The compounds of the present invention are to ion channels openers, more specifically, potassium channels openers. The compounds of the present are thus useful for treatment of various disorders including, but not limited to, urinary incontinence, overactive bladder, hypertension, erectile dysfunction, female sexual disorders, dysmenorrheal, irritable bowl syndrome, airway hyperactivity, epilepsy, stroke, Alzheimer's and Parkinson's diseases, myocardial injury, coronary artery disease, hair loss and baldness. Preferably, the compounds of the present invention are useful in the treatment of urinary incontinence or overactive bladder.

In an embodiment of the present invention, $R^1$ is selected from the group consisting of hydrogen, halogen, cyano, $CF_3$ and $-SO_2-CF_3$. In another embodiment of the present invention, $R^1$ is selected from the group consisting of halogen, cyano and $-SO_2-CF_3$. Preferably, $R^1$ is selected from the group consisting of fluoro, cyano and $-SO_2-CF_3$.

In an embodiment of the present invention, $R^2$ is selected from the group consisting of hydrogen, halogen, cyano, $CF_3$ and $-SO_2-CF_3$. In another embodiment of the present invention, $R^2$ is selected from the group consisting of hydrogen, cyano and $-SO_2-CF_3$. Preferably, $R^2$ is selected from the group consisting of hydrogen, cyano and $-SO_2-CF_3$.

In an embodiment of the present invention, a is 0. In another embodiment of the present invention, a is 1.

In an embodiment of the present invention, $L^1$ is selected from the group consisting of $-C(O)-$, $-CH(OH)-$ and $-C(O)-NR^4-$; wherein $R^4$ is selected from hydrogen or $C_{1-4}$alkyl. In another embodiment of the present invention, $L^1$ is selected from the group consisting of $-C(O)-$, $-CH(OH)-$ and $C(O)-NR^4-$; wherein $R^4$ is selected from hydrogen, methyl or ethyl. Preferably, $L^1$ is selected from the group consisting of $-C(O)-$, $-CH(OH)-$ and $-C(O)-NH-$.

In an embodiment of the present invention, $R^3$ is selected from the group consisting of hydrogen, $C_{1-4}$alkyl and aryl; wherein the aryl is optionally substituted with one or more independently selected from halogen, hydroxy, $C_{1-4}$alkyl, $C_{1-4}$alkoxy, cyano, nitro or $CF_3$. In another embodiment of the present invention, $R^3$ is selected from the group consisting of hydrogen, $C_{1-4}$alkyl, $-CH=CH-$, and aryl; wherein the aryl is optionally substituted with one or more independently selected from halogen. Preferably, $R^3$ is selected from the group consisting of hydrogen, methyl, $-CH=CH-$, 2-chlorophenyl, 3-chlorophenyl, 4-chlorophenyl, 2,3-dichlorophenyl, 2,4,-dichlrophenyl, 2,4,6-trichlorophenyl, 2-fluorophenyl and 2,4-difluorophenyl.

In an embodiment of the present invention, $R^3$ is other than hydrogen. In another embodiment of the present invention, $R^3$ is heteroaryl; wherein the heteroaryl is optionally substituted with one or more independently selected from halogen, hydroxy, $C_{1-4}$alkyl, $C_{1-4}$alkoxy, cyano, nitro or $CF_3$.

In an embodiment of the present invention, $L^1-R^3$ is MOM or SEM. Preferably, $L^1-R^3$ is MOM.

In an embodiment of the present invention, $R^4$ is selected from the group consisting of hydrogen, $-CH=CH-$, aryl and $-C(O)$-aryl; wherein the aryl, whether alone or as part of a substituent group, is optionally substituted with one or more independently selected from halogen, hydroxy, $C_{1-4}$alkyl, $C_{1-4}$alkoxy, cyano, nitro or $CF_3$. In another embodiment of the present invention, $R^4$ is selected from the group consisting of hydrogen, aryl and $-C(O)$-aryl; wherein the aryl is optionally substituted with one to two substituents independently selected from hydroxy, halogen, $C_{1-4}$alkoxy or cyano. Preferably, $R^4$ is selected from the group consisting of hydrogen, 2,4-dihydroxyphenyl, 2,4-dimethoxyphenyl, 2-hydroxy-4-cyano-phenyl and 4-chlorophenyl-carbonyl.

In another embodiment of the present invention, $R^4$ is selected from the group consisting of 6-membered heteroaryl and $-C(O)$-(6 membered heteroaryl); wherein the 6-membered heteroaryl, whether alone or as part of a substituent group, is optionally substituted with one or more independently selected from halogen, hydroxy, $C_{1-4}$alkyl, $C_{1-4}$alkoxy, cyano, nitro or $CF_3$.

In another embodiment of the present invention, is a compound selected from the group consisting of 3-(4-chlorobenzoyl)-4-methyl-2-oxo-2H-chromene-7-carbonitrile and pharmaceutically acceptable salts thereof.

In an embodiment of the present invention is any single compound or subset of compounds selected from the representative compounds listed in Tables 1 below.

Additional embodiments of the present invention, include those wherein the substituents selected for one or more of the variables defined herein (i.e. $R^1$, $R^2$, $R^3$, $R^4$, a and $L^1$) are independently selected to be any individual substituent or any subset of substituents selected from the complete list as defined herein.

Representative compounds of the present invention are as listed in Tables 1 below.

TABLE 1

![Structure: coumarin with R¹ at 7-position, R² at 6-position, CH₂-(L¹)ₐ-R³ at 4-position, R⁴ at 3-position]

| ID No. | R¹ | R² | (L¹)ₐ | R³ | R⁴ |
|---|---|---|---|---|---|
| 2 | —O—SO₂—CF₃ | H | —CH₂—O— | methyl | 2,4-dimethoxy-phenyl |
| 3 | cyano | H | absent (a = 0) | methyl | 4-chloro-phenyl-carbonyl- |
| 4 | cyano | H | —C(O)— | 4-chloro-phenyl | H |
| 6 | cyano | H | —CH₂—O— | methyl | 2,4-dimethoxy-phenyl |
| 7 | —O—SO₂—CF₃ | H | —CH₂—O— | H | 2,4-dihydroxy-phenyl |
| 8 | cyano | H | —CH₂—O— | H | 2,4-dihydroxy-phenyl |
| 9 | cyano | H | absent (a = 0) | allyl | 2,4-dihydroxy-phenyl |
| 11 | fluoro | H | absent (a = 0) | allyl | 2-hydroxy-4-cyano-phenyl |
| 12 | —O—SO₂—CF₃ | H | —CH(OH)— | 2,4-dichloro-phenyl | H |
| 13 | —O—SO₂—CF₃ | H | —C(O)—NH— | 2,4,6-trichloro-phenyl | H |
| 14 | cyano | H | —CH(OH)— | 2,4-dichloro-phenyl | H |
| 15 | cyano | H | —C(O)—NH— | 2,4-difluoro-phenyl | H |
| 16 | cyano | H | —C(O)—NH— | 2-fluoro-phenyl | H |
| 17 | cyano | H | —C(O)—NH— | 2-chloro-phenyl | H |
| 18 | cyano | H | —C(O)—NH— | 3-chloro-phenyl | H |
| 19 | cyano | H | —C(O)—NH— | 2,3-dichloro-phenyl | H |
| 20 | H | cyano | —CH(OH)— | 2,4-dichloro-phenyl | H |
| 21 | H | cyano | —C(O)— | 3-chloro-phenyl | H |
| 22 | H | —O—SO₂—CF₃ | —C(O)— | 3-chloro-phenyl | H |

As used herein, "halogen" shall mean chlorine, bromine, fluorine and iodine.

As used herein, the term "alkyl" whether used alone or as part of a substituent group, include straight and branched chains. For example, alkyl radicals include methyl, ethyl, n-propyl, isopropyl, n-butyl, isobutyl, sec-butyl, t-butyl, pentyl and the like. Similarly, the term "$C_{1-4}$alkyl" whether used alone or as part of a substituent group, include straight and branched chains containing 4 carbon atoms. For example, methyl, ethyl, n-propyl, isopropyl, n-butyl, isobutyl, sec-butyl and t-butyl.

As used herein, unless otherwise noted, "alkoxy" whether used alone or as part of a substituent group, shall denote an oxygen ether radical of the above described straight or branched chain alkyl groups. For example, methoxy, ethoxy, n-propoxy, sec-butoxy, t-butoxy, n-hexyloxy and the like. Similarly, the term "$C_{1-4}$alkoxy" whether used alone or as part of a substituent group, shall denote an oxygen ether radical of the above described straight or branched chain $C_{1-4}$alkyl groups. For example, methoxy, ethoxy, n-propoxy, sec-butoxy, t-butoxy, and the like.

As used herein, unless otherwise noted, "aryl" shall refer to unsubstituted carbocylic aromatic groups such as phenyl, naphthyl, and the like.

As used herein, unless otherwise noted, "heteroaryl" shall denote any five or six membered monocyclic aromatic ring structure containing at least one heteroatom selected from the group consisting of O, N and S, optionally containing one to three additional heteroatoms independently selected from the group consisting of O, N and S; or a nine or ten membered bicyclic aromatic ring structure containing at least one heteroatom selected from the group consisting of O, N and S, optionally containing one to four additional heteroatoms independently selected from the group consisting of O, N and S. The heteroaryl group may be attached at any heteroatom or carbon atom of the ring such that the result is a stable structure.

Examples of suitable heteroaryl groups include, but are not limited to, pyrrolyl, furyl, thienyl, oxazolyl, imidazolyl, purazolyl, isoxazolyl, isothiazolyl, triazolyl, thiadiazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, and the like. Preferred heteroaryl groups include pyrrolyl, pyridyl, pyrazolyl, pyrazinyl, and the like.

As used herein, the notation "*" shall denote the presence of a stereogenic center.

When a particular group is "substituted" (e.g., aryl, heterocycloalkyl, heteroaryl), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2$=CH—$CH_2$—, and the like; amides—groups of the formula —C(O)—R' wherein R' is for example methyl, phenyl, trifluoromethyl, and the like; N-sulfonyl derivatives—groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

Under standard nomenclature used throughout this disclosure, the terminal portion of the designated side chain is described first, followed by the adjacent functionality toward the point of attachment. Thus, for example, a "phenyl-alkyl-amino-carbonyl-alkyl" substituent refers to a group of the formula

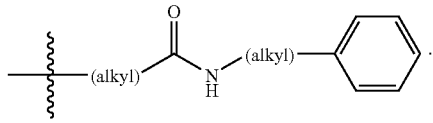

Abbreviations used in the specification, particularly the Schemes and Examples, are as follows
DIPEA=Diethylisopropylamine
DMF=N,N-Dimethylformamide
HEPES=4-(2-Hydroxyethyl)-1-Piperizine Ethane Sulfonic Acid
HPLC=High Pressure Liquid Chromatography
LiHMDS=Lithium Hexamethyldisilazinamide
MOM=Methoxy methyl
MOM-Br=Methoxy methyl bromide
MOM-Cl=Methoxy methyl chloride
Pd(PPh$_3$)$_4$ Palladium Tetrakis(triphenylphosphine)
SEM=2-(Trimethylsilyl)ethoxy methyl
SEM-Cl=2-(Trimethylsilyl)ethoxy methyl chloride
TEA or Et$_3$N=Triethylamine
Tf=Triflate (i.e. —$SO_2$—$CF_3$)
Tf$_2$O=Triflic anhydride
THF=Tetrahydrofuran The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

One skilled in the art will recognize that wherein a reaction step of the present invention may be carried out in a variety of solvents or solvent systems, said reaction step may also be carried out in a mixture of the suitable solvents or solvent systems.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases which may be used in the preparation of pharmaceutically acceptable salts include the following:

acids including acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydrocy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitric acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

Compounds of formula (I) may be prepared according to the process outlined in Scheme 1. More particularly, Scheme 1 outlines a process for attaching the -($L^1$)$_a$-$R^3$ and/or $R^4$ groups.

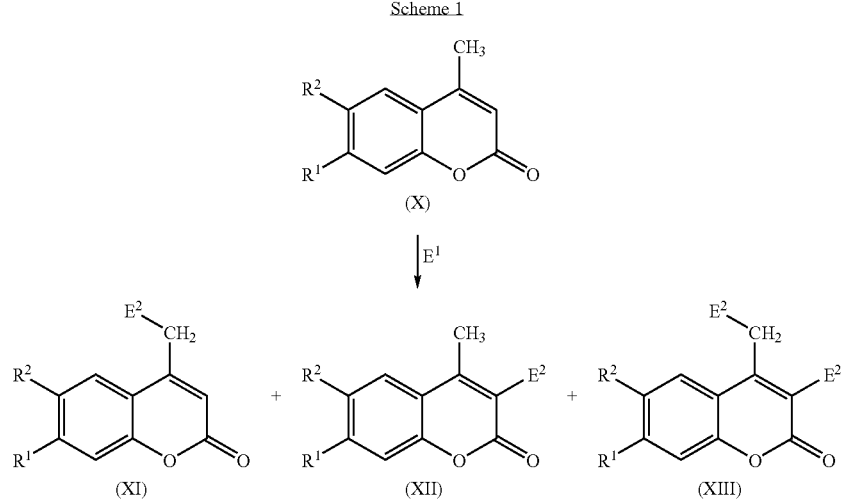

Accordingly, a suitably substituted compound of formula (X), a known compound or compound prepared by known methods, is reacted with a suitably substituted electrophile, designated as $E^1$, for example $R^3$—CHO, $R^4$—CHO, $R^3$—C(O)—Cl, $R^4$—C(O)—Cl, $R^3$—N=C=O, MOM-Cl, MOM-Br, SEM-Cl, and the like, to yield a mixture of the compounds of formula (XI), (XII) and (XIII), wherein $E^2$ is the corresponding substituent group.

For example, the table below lists the substituent group $E^2$ which is incorporated into the compounds of formula (XI), X(II) and (XIII) when the compound of formula (X) is reacted with the $E^1$ electrophiles listed above.

TABLE 2

| $E^1$ (Electrophile) | $E^2$ (Substituent Group) |
| --- | --- |
| $R^3$—CHO | —CH(OH)—$R^3$ |
| $R^4$—CHO | —CH(OH)—$R^4$ |
| $R^3$—C(O)—Cl | —C(O)—$R^3$ |
| $R^4$—C(O)—Cl | —C(O)—$R^4$ |
| $R^3$—N=C=O | —C(O)—NH—$R^3$ |
| MOM-Cl or MOM-Br | MOM |
| SEM-Cl or SEM-Br | SEM |

One skilled in the art will recognize that depending on the choice of electrophile $E^1$, the compounds of formula (XI), (XII) and/or (XIII) may correspond to compounds of formula (I).

Preferably, the mixture of compounds of formula (XI), (XII) and (XIII) is separated, according to known methods, for example by column chromatography.

One skilled in the art will further recognize that compounds of formula (I) wherein the -($L^1$)$_a$-$R^3$ and/or $R^4$ groups are different may be prepared according to the process outlined in Scheme 1, repeating the process as necessary, and selecting and substituting suitably substituted starting materials for the compound of formula (X) and the $E^1$ reactant as appropriate.

One skilled in the art will further recognize that compounds of formula (I) wherein $L^1$ is present and is —C(O)—$NR^A$— and wherein $R^A$ is other than hydrogen may be prepared from the corresponding compound of formula (I) wherein $R^A$ is hydrogen by reacting with a suitably selected alkylating agent, according to known methods.

Compounds of formula (I) wherein $R^4$ is selected from aryl or a 6-membered heteroaryl group are similarly prepared according to the process outlined in Scheme 1 above, substituting a suitably substituted compound of formula (XIV)

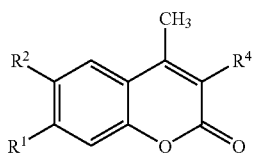

(XIV)

for the compound of formula (X).

Compounds of formula (X) or compounds of formula (I) wherein $R^1$ and/or $R^2$ are selected from —O—$SO_2$—$CF_3$ or CN may be prepared from the corresponding compound of formula (X) or compound of formula (I) wherein the corresponding $R^1$ and/or $R^2$ group(s) are OH, as outlined in Scheme 2. For illustration purposes, Scheme 2 is shown as the process would be applied to the representative compound of formula (Ia).

Scheme 2

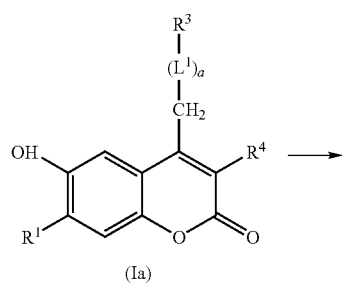

(Ia)

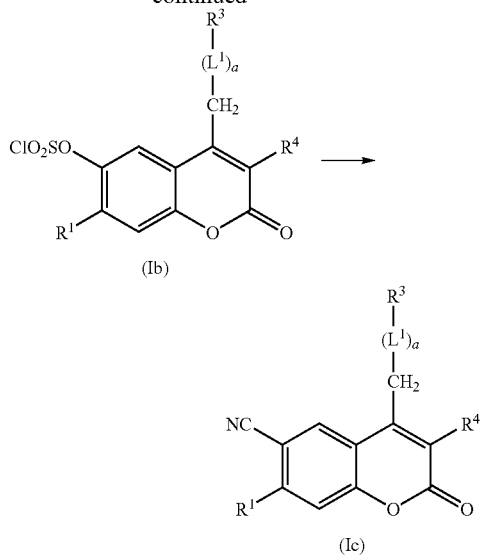

Accordingly, a suitably substituted compound of formula (Ia), a known compound or compound prepared by known methods, is reacted with triflate anhydride, a known compound, in the presence of a tertiary amine base such as TEA, DIPEA, pyridine, and the like, preferably pyridine, in an organic solvent such as methylene chloride, chloroform, and the like, to yield the corresponding compound of formula (Ib).

The compound of formula (Ib) is reacted with $Zn(CN)_2$, sodium cyanide, potassium cyanide and the like, in an organic solvent such as DMF, THF, toluene, and the like, at an elevated temperature in the range of about 60° C. to about 150° C., to yield the corresponding compound of formula (Ic).

Compounds of formula (I) wherein -$L^1$-$R^3$ is allyl may be prepared according to the process outlined in Scheme 3.

Scheme 3

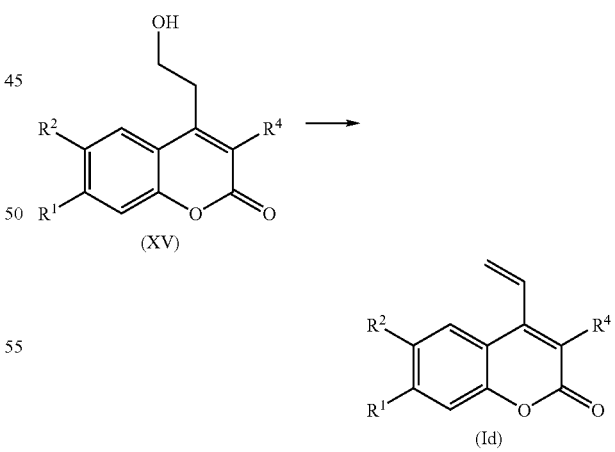

More specifically, a suitably substituted compound of formula (XV), a known compound or compound prepared by known methods, is reacted according to known methods (for example by subjecting to heat) to yield the corresponding compound of formula (Id).

The present invention further comprises pharmaceutical compositions containing one or more compounds of formula (I) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more of the compounds of the present invention selected as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 50-100 mg and may be given at a dosage of from about 0.5-5.0 mg/kg/day, preferably from about 1.0-3.0 mg/kg/day. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating disorders related to ion channels, for example potassium ion channels, described in the present invention may also be carried out using a pharmaceutical composition comprising any of the compounds as defined herein and a pharmaceutically acceptable carrier. The pharmaceutical composition may contain between about 0.01 mg and 1000 mg, preferably about 1 to 500 mg, more preferably, 10 to 100 mg of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methylcellulose and the like. For parenteral administration, sterile suspensions and solutions are desired. Isotonic preparations which generally contain suitable preservatives are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxy-ethylaspartamidephenol, or polyethyl eneoxidepolylysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of disorders related to ion channels, for example potassium ion channels, is required.

The daily dosage of the products may be varied over a wide range from 0.01 to 1,000 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250, 500 and 1000 milligrams of the active ingredient for the symptomatic adjustment of the dosage to the patient to be treated. An effective amount of the drug is ordinarily supplied at a dosage level of from about 0.01 mg/kg to about 300 mg/kg of body weight per day. Preferably, the range is from about 0.5 to about 5.0 mg/kg of body weight per day, most preferably, from about 1.0 to about 3.0 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The following Examples are set forth to aid in the understanding of the invention, and are not intended and should not be construed to limit in any way the invention set forth in the claims which follow thereafter.

Example 1

Trifluoro-methanesulfonic acid 3-(2,4-dimethoxy-phenyl)-4-(2-methoxy-ethyl)-2-oxo-2H-chromen-7-yl ester (Compound #2)

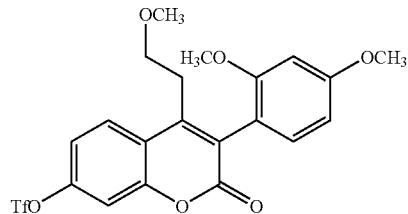

3-(2,4-Dimethoxy-phenyl)-7-hydroxy-4-(2-methoxy-ethyl)-chromen-2-one (1.8 g, 5.2 mmol) and pyridine (30 mL) were dissolved in $CH_2Cl_2$ (200 mL) at room temperature and the reaction mixture was cooled to 0° C., then treated with $Tf_2O$ (1.3 mL). After 1 hour, ethyl acetate (200 mL) was poured into the reaction mixture and the reaction mixture was transferred into a separation funnel. The reaction mixture was then washed with 5% sodium bicarbonate (2×250 ml), water (250 ml) and then brine. The organic layer was dried over sodium sulfate and concentrated. Flash column chromatography on silica gel eluted with 20-50% ethyl acetate in hexane yielded the title compound as a yellow solid.

m/z=489 (M+H$^+$)

Example 2

4-[2-(4-Chloro-phenyl)-2-oxo-ethyl]-2-oxo-2H-chromene-7-carbonitrile (Compound #4) and 3-(4-Chloro-benzoyl)-4-methyl-2-oxo-2H-chromene-7-carbonitrile (Compound #3)

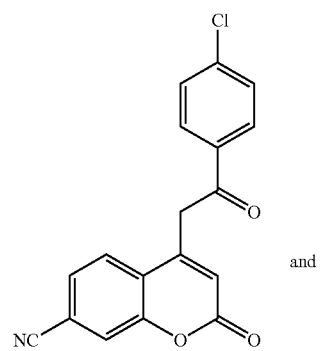

and

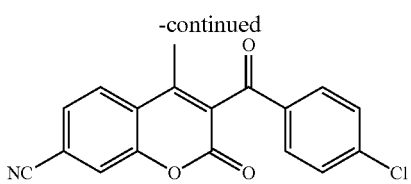

To a solution of 4-methyl-2-oxo-2H-chromene-7-carbonitrile (170 mg, 0.918 mmol) in dry THF (5 mL) at −20° C. was added drop wise 1.0 M LiHMDS solution in THF (1 mL). After 30 minutes 4-chloro-benzoyl chloride (160 μL) was added slowly and the reaction mixture was stirred for 1 hour. The reaction mixture was then quenched with saturated aqueous ammonium chloride (10 mL) and extracted with ethyl acetate (50 mL). The organic layer was separated and dried over sodium sulfate, then concentrated and purified on silica gel eluted with 30% ethyl acetate in hexanes to yield the title compounds as a white foam and a white solid, respectively.

4-[2-(4-Chloro-phenyl)-2-oxo-ethyl]-2-oxo-2H-chromene-7-carbonitrile m/z=324 (M+H+)

3-(4-Chloro-benzoyl)-4-methyl-2-oxo-2H-chromene-7-carbonitrile m/z=324 (M+H+)
$^1$HNMR (CDCl$_3$, 400 MHz) δ (ppm) 7.8 (m, 2H), 7.65 (s, 1H), 7.8 (d, J=8.4 Hz, 1H), 7.4 (d, J=8.4 Hz, 2H), 6.3 (dd, $^1$J=8.4 Hz, $^2$J=2 Hz, 1H), 2.4 (s, 3H).

Example 3

3-(2,4-Dimethoxy-phenyl)-4-(2-methoxy-ethyl)-2-oxo-2H-chromene-7-carbonitrile (Compound #6)

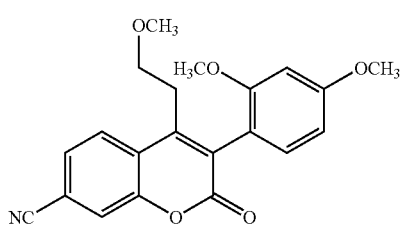

Trifluoro-methanesulfonic acid 3-(2,4-dimethoxy-phenyl)-4-(2-methoxy-ethyl)-2-oxo-2H-chromen-7-yl ester (862 mg, 1.766 mol), Zn (CN)$_2$ (310 mg) and Pd(PPh$_3$)$_4$ (204 mg) were dissolved in DMF (12 mL) at room temperature in a sealed tube. After 10 min, the reaction mixture was heated to 150° C. for 4 h. The reaction mixture was cooled to room temperature and ethyl acetate (200 mL) was added. The reaction mixture was then poured into a separation funnel, washed with water (2×100 ml) and brine (2×100 ml). The organic layer was dried over sodium sulfate and concentrated. The product was purified on silica gel eluted with 30-50% ethyl acetate in hexanes to yield 3-(2,4-Dimethoxy-phenyl)-4-(2-methoxy-ethyl)-2-oxo-2H-chromene-7-carbonitrile as a slightly yellow solid.

M/z=489 (M+H+)
$^1$HNMR (CDCl$_3$, 400 MHz) δ (ppm) 7.85 (d, J=6.0 Hz, 1H), 7.65 (s, 1H), 7.55 (d, J=6.0 Hz, 1H), 7.1 (d, J=6.1 Hz, 1H), 6.5 (m, 2H), 3.85 (s, 3H), 3.75 (s, 3H), 3.43 (m, 2H), 2.95 (m, 2H).

Example 4

Trifluoro-methanesulfonic acid 3-(2,4-dihydroxy-phenyl)-4-(2-hydroxy-ethyl)-2-oxo-2H-chromen-7-yl ester (Compound #7)

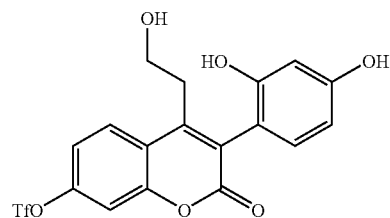

Trifluoro-methanesulfonic acid 3-(2,4-dimethoxy-phenyl)-4-(2-methoxy-ethyl)-2-oxo-2H-chromen-7-yl ester (450 mg, 0.92 mol) was dissolved in CH$_2$Cl$_2$ (10 mL) at room temperature in a 200 ml round bottom flask. The reaction mixture was then cooled to −30° C., and BBr$_3$ (1.8 ml) was added and the reaction mixture stirred at room temperature for 4 h. The reaction mixture was cooled to 0° C. and water (40 mL) was added, followed by ethyl acetate (50 mL). The reaction mixture was then poured into a separation funnel. The organic layer was separated and washed with water (1×40 ml) and brine (1×30 ml). The organic layer was dried over sodium sulfate and concentrated. The product was purified on silica gel eluted with 50%-100% ethyl acetate in hexanes to yield trifluoro-methanesulfonic acid 3-(2,4-dihydroxy-phenyl)-4-(2-hydroxy-ethyl)-2-oxo-2H-chromen-7-yl ester as a light yellow foam M/z=447 (M+H+), 469 (M+Na)
$^1$HNMR (CDCl$_3$, 400 MHz) δ (ppm) 7.91 (d, J=6.0 Hz, 1H), 7.25-7.35 (m, 3H), 6.85 (d, J=6.0 Hz, 1H), 6.4-6.5 (m, 2H), 3.8 (m, 2H), 3.75 (s, 2.95-3.2 (m, 5H, 3H exchangeable with D$_2$O).

Example 5

3-(2,4-Dihydroxy-phenyl)-4-(2-hydroxy-ethyl)-2-oxo-2H-chromene-7-carbonitrile (Compound #8)
and 3-(2,4-Dihydroxy-phenyl)-2-oxo-4-vinyl-2H-chromene-7-carbonitrile (Compound #9)

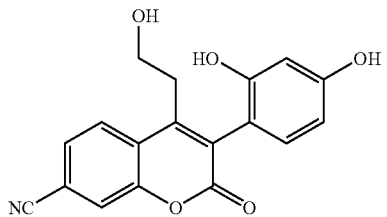

and

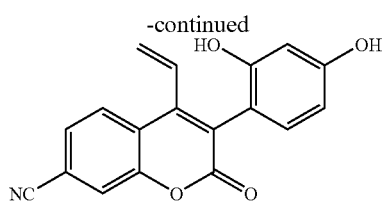

3-(2,4-Dimethoxy-phenyl)-4-(2-methoxy-ethyl)-2-oxo-2H-chromene-7-carbonitrile (380 mg, 1.04 mmol) was dissolved in $CH_2Cl_2$ (12 mL) at room temperature in a 200 ml round bottom flask. The reaction mixture was then cooled to −30° C., and $BBr_3$ (1.8 ml) was added, then the reaction mixture was stirred at room temperature for 4 h. The reaction mixture was cooled to 0° C. and water (40 mL) was added, followed by ethyl acetate (50 mL). The reaction mixture was then poured into a separation funnel. The organic layer separated and washed with water (1×40 ml) and brine (1×30 ml). The organic layer was dried over sodium sulfate and concentrated. The product was purified on silica gel eluted with 50%-100% ethyl acetate in hexanes to yield the title compounds as a foam and a yellow solid, respectively.

3-(2,4-Dihydroxy-phenyl)-2-oxo-4-vinyl-2H-chromene-7-carbonitrile m/z=306 (M+H+)

3-(2,4-Dihydroxy-phenyl)-4-(2-hydroxy-ethyl)-2-oxo-2H-chromene-7-carbonitrile

M/z=324 (M+H+)

Example 6

8-Fluoro-5-oxo-11,12-dihydro-5H-6,13-dioxa-benzo[3,4]cyclohepta[2-a]naphthalene-2-carbonitrile and 44-(7-Fluoro-2-oxo-4-vinyl-2H-chromen-3-yl)-3-hydroxy-benzonitrile (Compound #11)

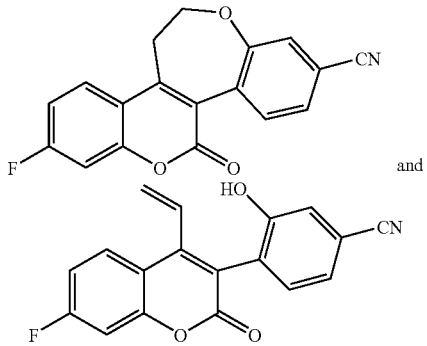

Trifluoro-methanesulfonic acid 8-fluoro-5-oxo-4b,10b,11,12-tetrahydro-5H-6,13-dioxa-benzo[3,4]cyclohepta[1,2-a]naphthalen-2-yl ester (450 mg, 1.046 mmol), Zn $(CN)_2$ (183 mg) and $Pd(PPh_3)_4$ (120 mg) were dissolved in DMF (12 mL) at room temperature in a sealed tube. After 10 min. the reaction mixture was heated to 150° C. for 4 h. The reaction mixture was cooled to room temperature and ethyl acetate (200 mL) was added. The reaction mixture was then poured into a separation funnel, washed with water (2×100 ml) and brine (2×100 ml). The organic layer was dried over sodium sulfate and concentrated. The product was purified on silica gel eluted with 30-50% ethyl acetate in hexanes to yield the title compounds as a thick yellow oil and as a brown semi-solid, respectively.

8-Fluoro-5-oxo-4b,10b,11,12-tetrahydro-5H-6,13-dioxa-benzo[3,4]cyclohepta[1,2-a]naphthalene-2-carbonitrile M/z=310 (M+H+)
$^1$HNMR ($CDCl_3$, 400 MHz) δ (ppm) 7.85 (d, J=6.0 Hz, 1H), 7.75-7.55 (m, J=6.0 Hz, 2H), 7.1-7.22 (m, J=6.1 Hz, 3H), 4.75 (t, 2H), 3.05 (t, 3H)

4-(7-Fluoro-2-oxo-4-vinyl-chroman-3-yl)-3-hydroxy-benzonitrile

M/z=310 (M+H+)
$^1$HNMR ($CDCl_3$, 400 MHz) δ (ppm) 7.83 (m, 2H), 7.1-7.3 (m, 4H), 6.5 (dd, J=8 Hz, 6 Hz, 1H), 6.25 (bs, 1H), 5.6 (d, J=10 Hz, 1H), 5.4 (d, J=10 Hz, 1H).

Example 7

Trifluoro-methanesulfonic acid 4-[2-(2,4-dichloro-phenyl)-2-hydroxy-ethyl]-2-oxo-2H-chromen-7-yl ester (Compound #12)

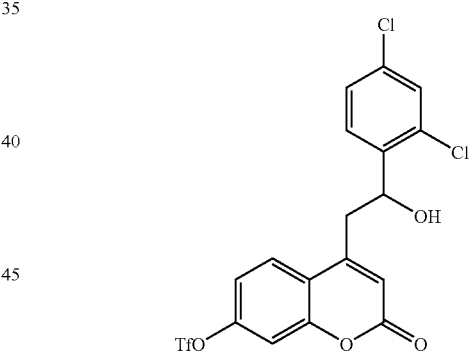

To a solution of Trifluoro-methanesulfonic acid 4-methyl-2-oxo-2H-chromen-7-yl ester (340 mg, 1.1 mmol) in dry THF (8 mL0 at −20° C. was added drop wise 1.0 M LiHMDS solution in THF (1.2 mL). After 30 minutes 2,4-dichloro-benzaldehyde (130 μL) was added slowly into the reaction mixture and the reaction mixture was stirred for 1 hour. The reaction mixture was quenched with saturated aqueous ammonium chloride (10 mL) and extracted with ethyl acetate (50 mL). The organic layer was separated and dried over sodium sulfate, concentrated and purified on silica gel eluted with 30% ethyl acetate in hexanes to yield trifluoro-methanesulfonic acid 4-[2-(2,4-dichloro-phenyl)-2-hydroxy-ethyl]-2-oxo-2H-chromen-7-yl ester as a light yellow solid.

m/z 484 (M+H+)
$^1$ HNMR ($CDCl_3$, 400 MHz) δ (ppm) 7.9 (d, J=6 Hz, 1H), 7.6 Hz (d, J=6 Hz, 1H), 7.1-7.4 (m, 4H), 6.45 (s, 1H), 5.45 (m, 1H), 2.95-3.1 (m, 2H).

Example 8

4-[2-(2,4-Dichloro-phenyl)-2-hydroxy-ethyl]-2-oxo-2H-chromene-7-carbonitrile (Compound #14)

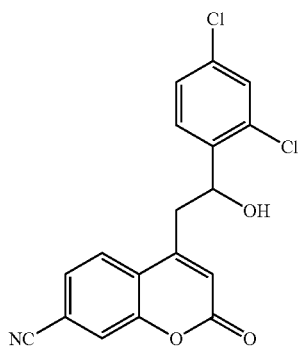

To a solution of 4-methyl-2-oxo-2H-chromene-7-carbonitrile (76 mg, 0.427 mmol) in dry THF (4 mL) at −20° C. was added drop wise 1.0 M LiHMDS solution in THF (0.52 mL). After 30 minutes 2,4-dichloro-benzaldehyde (60 μL) was added slowly into the reaction mixture and then stirred for 1 hour. The reaction mixture was then quenched with saturated aqueous ammonium chloride (2 mL) and extracted with ethyl acetate (50 mL). The organic layer was separated and dried over sodium sulfate, then concentrated and purified on silica gel eluted with 30% ethyl acetate in hexanes to yield 4-[2-(2,4-dichloro-phenyl)-2-hydroxy-ethyl]-2-oxo-2H-chromene-7-carbonitrile as a yellow solid.

m/z 382 (M+Na+)

[1] HNMR (CDCl$_3$, 400 MHz) δ (ppm) 7.8 (d, J=6.6 Hz, 1H), 7.3-7.7 Hz (m, 5H), 6.55 (s, 1H), 5.42 (m, 1H), 2.85-3.1 (m, 2H).

Example 9

2-(7-Cyano-2-oxo-2H-chromen-4-yl)-N-(2,4-difluoro-phenyl)-acetamide (Compound #15)

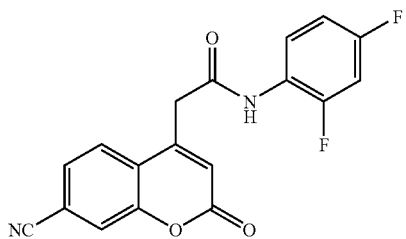

To a solution of 4-methyl-2-oxo-2H-chromene-7-carbonitrile (671 mg, 3.62 mmol) in dry THF (30 mL) at −20° C. was added drop wise 1.0 M LiHMDS solution in THF (5.4 mL). After 30 minutes 2,4-difluoro-1-isocyanato-benzene (224 mg) was added into the reaction mixture and the reaction mixture was then stirred for 1 hour. The reaction mixture was quenched with saturated aqueous ammonium chloride (25 mL) and extracted with ethyl acetate (50 mL). The organic layer was separated and dried over sodium sulfate, then concentrated and purified on silica gel eluted with 30%-100% ethyl acetate in hexanes to yield 2-(7-cyano-2-oxo-2H-chromen-4-yl)-N-(2,4-difluoro-phenyl)-acetamide as a yellow solid.

M/z=341 (M+H+) 363 (M+Na+)

[1] HNMR (DMSO, 400 MHz) δ (ppm) 10.6 (bs, 1H), 7.65 (s, 1H), 7.52 (d, J=8.1 Hz, 1H), 7.45 (m, 1H), 6.8-7.25 (m, 3H), 6.45 (s, 1H), 3.72 (bs2H).

Example 10

2-(7-Cyano-2-oxo-2H-chromen-4-yl)-N-(2-fluoro-phenyl)-acetamide (Compound #16)

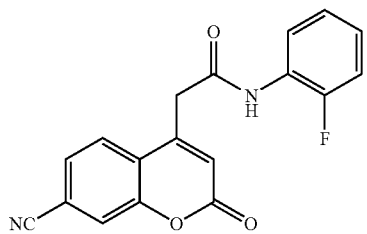

To a solution of 4-methyl-2-oxo-2H-chromene-7-carbonitrile (670 mg, 3.6 mmol) in dry THF (30 mL) at −20° C. was added drop wise 1.0 M LiHMDS solution in THF (5.4 mL). After 30 minutes 2-fluoro-1-isocyanato-benzene (189 mg) was added into the reaction mixture and the reaction mixture was stirred for 1 hour. The reaction mixture was then quenched with saturated aqueous ammonium chloride (25 mL) and extracted with ethyl acetate (50 mL). The organic layer was separated and dried over sodium sulfate, then concentrated and purified on silica gel eluted with 30%-100% ethyl acetate in hexanes to yield 2-(7-cyano-2-oxo-2H-chromen-4-yl)-N-(2-fluoro-phenyl)-acetamide as a solid.

M/z=323 (M+H+).

[1] HNMR (CDCl$_3$, 400 MHz) δ (ppm) 11.2 (bs, 1H), 7.7 (s, 1H), 7.5-7.1 (m, 5H), 6.35 (s, 1H), 3.81 (bs, 2H).

Example 11

N-(3-Chloro-phenyl)-2-(7-cyano-2-oxo-2H-chromen-4-yl)-acetamide (Compound #18)

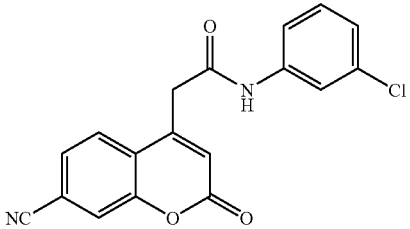

To a solution of 4-methyl-2-oxo-2H-chromene-7-carbonitrile (673 mg, 3.6 mmol) in dry THF (30 mL) at −20° C. was added drop wise 1.0 M LiHMDS solution in THF (5.4 mL). After 30 minutes 3-chloro-1-isocyanato-benzene (222.3 mg) was added into the reaction mixture and the reaction mixture was stirred for 1 hour. The reaction mixture was then quenched with saturated aqueous ammonium chloride (25 mL) and extracted with ethyl acetate (50 mL). The organic layer was separated and dried over sodium sulfate, then concentrated and purified on silica gel eluted with 30%-100% ethyl acetate in hexanes to yield 2-(7-cyano-2-oxo-2H-chromen-4-yl)-N-(3-chloro-phenyl)-acetamide as a yellow solid.

M/z=339 (M+H+) 361 (M+Na+).

Example 12

N-(2-Chloro-phenyl)-2-(7-cyano-2-oxo-2H-chromen-4-yl)-acetamide (Compound #17)

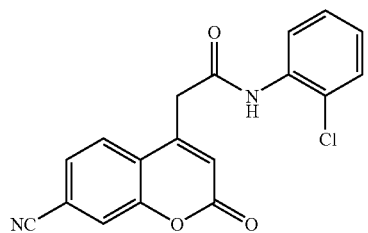

To a solution of 4-methyl-2-oxo-2H-chromene-7-carbonitrile (670 mg, 3.6 mmol) in dry THF (30 mL) at −20° C. was added drop wise 1.0 M LiHMDS solution in THF (5.4 mL). After 30 minutes 2-chloro-1-isocyanato-benzene (221 mg) was added into the reaction mixture and the reaction mixture was stirred for 1 hour. The reaction mixture was then quenched with saturated aqueous ammonium chloride (25 mL) and extracted with ethyl acetate (50 mL). The organic layer was separated and dried over sodium sulfate, then concentrated and purified on silica gel eluted with 30%-100% ethyl acetate in hexanes to yield 2-(7-cyano-2-oxo-2H-chromen-4-yl)-N-(2-chloro-phenyl)-acetamide as a foam.

M/z=339 (M+H+) 361 (M+Na+).

Example 13

2-(7-Cyano-2-oxo-2H-chromen-4-yl)-N-(2,3-dichloro-phenyl)-acetamide (Compound #19)

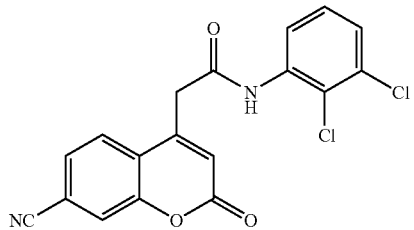

To a solution of 4-methyl-2-oxo-2H-chromene-7-carbonitrile (673 mg, 3.6 mmol) in dry THF (30 mL) at −20° C. was added drop wise 1.0 M LiHMDS solution in THF (5.4 mL). After 30 minutes 2-chloro-1-isocyanato-benzene (272 mg) was added into the reaction mixture and the reaction mixture was stirred for 1 hour. The reaction mixture was then quenched with saturated aqueous ammonium chloride (25 mL) and extracted with ethyl acetate (50 mL). The organic layer was separated and dried over sodium sulfate, then concentrated and purified on silica gel eluted with 30%-100% ethyl acetate in hexanes to yield 2-(7-cyano-2-oxo-2H-chromen-4-yl)-N-(2,3-dichloro-phenyl)-acetamide as a foam.

M/z=373 (M+H+) 395 (M+Na+).

Example 14

Trifluoro-methanesulfonic acid 4-methyl-2-oxo-2H-chromen-6-yl ester

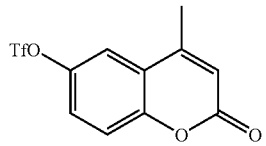

6-Hydroxy-4-methyl-chromen-2-one (25 mg, 0.142 mol) and pyridine (300 mL) were dissolved in $CH_2Cl_2$ (200 mL) at room temperature and the reaction mixture was cooled to 0° C. and then treated with $Tf_2O$ (40 mL). After 1 hour, ethyl acetate (900 mL) was poured into the reaction mixture and the reaction mixture was transferred into a separation funnel. The reaction mixture was then washed with 5% sodium bicarbonate (2×450 ml), water (450 ml) and then brine. The organic layer was dried over sodium sulfate and concentrated. Flash column chromatography on silica gel eluted with 20-50% ethyl acetate in hexane yielded the title compound as a foam.

M/z 309 (M+H+)

[1] HNMR ($CDCl_3$, 400 MHz) δ (ppm) 7.6 (d, J=4 Hz, 1H)), 7.45 (d, J=4 Hz, 1H), 7.25 (s, 1H), 6.45 (s, 1H), 2.5 (s, 3H)

Example 15

4-Methyl-2-oxo-2H-chromene-6-carbonitrile

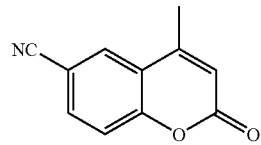

Trifluoro-methanesulfonic acid 4-methyl-2-oxo-2H-chromen-6-yl ester (10.38 mg, 33.7 mmol), Zn $(CN)_2$ (4.7 g) and $Pd(PPh_3)_4$ (3.8 g) were dissolved in DMF (200 mL) at room temperature in a sealed tube. After 10 min, the reaction mixture was heated to 150° C. for 4 h. The reaction mixture was then cooled to room temperature and ethyl acetate (800 mL) was added. The reaction mixture was then poured into a separation funnel, washed with water (2×400 ml) and brine (2×600 ml). The organic layer was dried over sodium sulfate and concentrated. The product was purified on silica gel eluted with 30-80% ethyl acetate in hexanes to yield 4-methyl-2-oxo-2H-chromene-6-carbonitrile as a white powder.

M/z 186 (M+H+)

[1] HNMR (DMSO, 400 MHz) δ (ppm) 8.41 (s, 1H), 8.05 (d, J=6 Hz, 1H), 7.6 (d, 6 Hz, 1H), 6.5 (s, 1H). 2.6 (s, 3H)

Example 16

4-[2-(2,4-Dichloro-phenyl)-2-hydroxy-ethyl]-2-oxo-2H-chromene-6-carbonitrile (Compound #20)

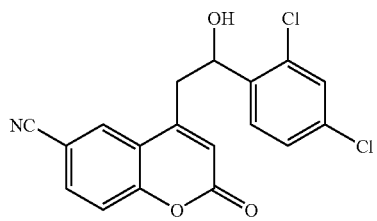

To a solution of 4-methyl-2-oxo-2H-chromene-6-carbonitrile (56 mg, 0.325 mmol) in dry THF (12 mL) at −20° C. was added drop wise 1.0 M LiHMDS solution in THF (0.6 mL). After 30 minutes 2,4-dichlorobenzaldehyde (105 mg) was added into the reaction mixture and the reaction mixture was stirred for 1 hour. The reaction mixture was then quenched with saturated aqueous ammonium chloride (10 mL) and extracted with ethyl acetate (50 mL). The organic layer was separated and dried over sodium sulfate, then concentrated and purified on silica gel eluted with 30%-60% ethyl acetate in hexanes to yield 4-[2-(2,4-dichloro-phenyl)-2-hydroxy-ethyl]-2-oxo-2H-chromene-6-carbonitrile as a white powder.

M/z=360 (M+H$^+$) 382 (M+Na$^+$)

$^1$ HNMR (DMSO, 400 MHz) δ (ppm) 8.43 (s, 1H), 8.15 (d, J=6 Hz, 1H), 7.7 (d, 6 Hz, 1H), 7.65 (m, 2H), 7.50 (d, J=6.2 Hz, 1H), 6.45 (s, 1H). 5.8 (d, 1H), 5.24 m, 1H), 3.12 (m, 2H)

Example 17

4-[2-(3-Chloro-phenyl)-2-oxo-ethyl]-2-oxo-2H-chromene-6-carbonitrile (Compound #21)

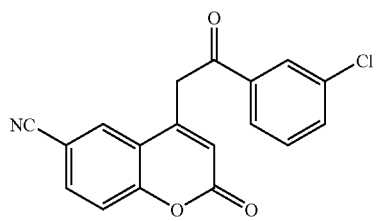

To a solution of 4-methyl-2-oxo-2H-chromene-6-carbonitrile (180 mg, 0.92 mmol) in dry THF (33 mL) at −20° C. was added drop wise 1.0 M LiHMDS solution in THF (1.6 mL). After 30 minutes 3-chlorobenzoylchloride (200 mg) was added into the reaction mixture and the reaction mixture was stirred for 1 hour. The reaction mixture was then quenched with saturated aqueous ammonium chloride (15 mL) and extracted with ethyl acetate (50 mL). The organic layer was separated and dried over sodium sulfate, then concentrated and purified on silica gel eluted with 30%-60% ethyl acetate in hexanes to yield 4-[2-(3-chloro-phenyl)-2-oxo-ethyl]-2-oxo-2H-chromene-6-carbonitrile as a white solid.

M/z=324 (M+H$^+$) 346 (M+Na$^+$).

Example 18

Trifluoro-methanesulfonic acid 4-[2-(3-chloro-phenyl)-2-oxo-ethyl]-2-oxo-2H-chromen-6-yl ester (Compound #22)

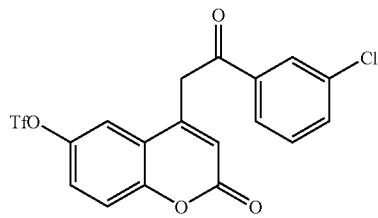

To a solution of 4-methyl-2-oxo-2H-chromene-6-carbonitrile (330 mg, 1.07 mmol) in dry THF (33 mL) at −20° C. was added drop wise 1.0 M LiHMDS solution in THF (1.6 mL). After 30 minutes 3-chlorobenzoylchloride (110 mg) was added into the reaction mixture and the reaction mixture stirred for 1 hour. The reaction mixture was then quenched with saturated aqueous ammonium chloride (15 mL) and extracted with ethyl acetate (50 mL). The organic layer was separated and dried over sodium sulfate, then concentrated and purified on silica gel eluted with 30%-60% ethyl acetate in hexanes to yield trifluoro-methanesulfonic acid 4-[2-(3-Chloro-phenyl)-2-oxo-ethyl]-2-oxo-2H-chromene-6-carbonitrile as a foam.

M/z=447 (M+H$^+$) 469 (M+Na$^+$)

$^1$ HNMR (CDCl$_3$, 400 MHz) δ (ppm) 8.01 (s, 1H), 7.9 (d, J=6 Hz, 1H), 7.61 (d, 6 Hz, 1H), 7.2-7.5 (m, 4H), 6.45 (s, 1H). 4.4 (s, 2H)

Example 19

Trifluoro-methanesulfonic acid 2-oxo-4-[(2,4,6-trichloro-phenylcarbamoyl)-methyl]-2H-chromen-7-yl ester (Compound #13)

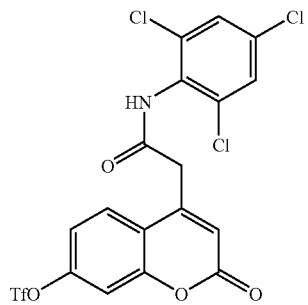

To a solution of trifluoro-methanesulfonic acid 4-methyl-2-oxo-2H-chromen-7-yl ester (285 mg, 1.54 mmol) in dry THF (50 mL) at −20° C. was added dropwise 1.0 M LiHMDS solution in THF (2.1 mL). After 30 minutes 2,4,5-trichlorophenylisocynate (342 mg) was added into the reaction mixture and the reaction mixture was stirred for 1 hour. The reaction mixture was then quenched with saturated aqueous ammonium chloride (32 mL) and extracted with ethyl acetate (50 mL). The organic layer was separated, dried over sodium sulfate, concentrated and purified on silica gel eluted with 30%-80% ethyl acetate in hexanes to yield the title compound as a yellow foam.

m/z=529 (M+H+), 551 (M+Na+)

[1] HNMR (CDCl₃, 400 MHz) δ (ppm) 7.9 (d, J=6 Hz, 1H), 7.45 (s, 2H), 7.2-7.5 (m, 3H), 6.55 (s, 1H). 3.89 (s, 2H)

Example 20

Potassium Channel Assay

TE671 human medulloblastoma cells were obtained from ATCC and grown in Dulbecco's modified Eagle's medium (DMEM) supplemented with 10% fetal bovine serum, 100 U/ml penicillin and 100 U/ml streptomycine.

The day before testing, the cells were plated in black 96-well plates at 50K/well. On the day of testing, the growth media was removed, then 100 μl of FLIPR buffer (20 mM HEPES, 120 mM NaCl, 2 mM KCl, 2 mM CaCl2, 1 mM MgCl2, 5 mM Glucose) and 100 μl of Membrane Potential Assay Dye (Molecular Devices) dissolved in FLIPR buffer were added to each well. The cells were incubated at room temperature for 15 to 30 min.

The effect of test compounds on KATP channels were evaluated on a fluorometric imaging plate reader (FLIPR, Molecular Devices) at room temperature. After a baseline period, 50 μl of 5× stock solution of test compound prepared in FLIPR buffer was added and fluorescent change was monitored for 3 minutes. After this reading, glyburide, a KATP channel blocker, was added to a final concentration of 5 μM to check the specificity of the test compound as a KATP channel openers. Hyperpolarization resulting from KATP channel opening was observed as a decrease in fluorescent intensity.

Representative compounds of the present invention were tested according to the procedure described above, with results as listed in Table 3 below.

TABLE 3

| ID No. | EC$_{50}$ (μM) |
|---|---|
| 2 | 9.55 |
| 3 | >30 |
| 4 | 15.87 |
| 5 | 12.21 |
| 6 | >30 |
| 7 | 19.46 |
| 8 | 23.22 |
| 9 | 3.29 |
| 11 | >30 |
| 12 | 6.58 |
| 13 | 8.76 |
| 14 | >30 |
| 15 | 13.89 |
| 16 | 3.84 |
| 17 | 19.45 |
| 18 | 7.74 |
| 19 | 10.72 |
| 20 | >30 |
| 21 | >30 |
| 22 | 19.90 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A compound of formula (I)

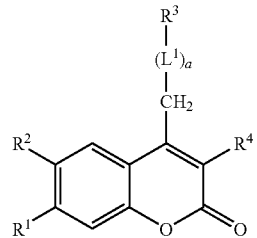

wherein
$R^1$ is selected from the group consisting of hydrogen, halogen, cyano, nitro, $CF_3$ and —O—$SO_2$—$CF_3$;
$R^2$ is selected from the group consisting of hydrogen, halogen, cyano, nitro, $CF_3$ and —O—$SO_2$—$CF_3$;
provided that $R^1$ and $R^2$ are not each hydrogen;
a is an integer from 0 to 1;
$L^1$ is selected from the group consisting of —C(O)—, —CH(OH)— and —C(O)—$NR^A$—; wherein $R^A$ is selected from hydrogen or $C_{1-4}$alkyl;
$R^3$ is selected from the group consisting of hydrogen, $C_{1-4}$alkyl, $C_2$alkenyl, aryl and heteroaryl; wherein the aryl or heteroaryl is optionally substituted with one or more substituents independently selected from halogen, hydroxy, $C_{1-4}$alkyl, $C_{1-4}$alkoxy, cyano, nitro or $CF_3$;
alternatively, -$L^1$-$R^3$ is selected from methoxy methyl or 2-(Trimethylsilyl)ethoxy methyl;
provided that when a is 0, then $R^3$ is other than hydrogen or $C_{1-4}$alkyl;
provided further that when a is 1 and $L^1$ is —CH(OH)—, then $R^3$ is other than hydrogen;
$R^4$ is selected from the group consisting of hydrogen, aryl, —C(O)-aryl, 6-membered heteroaryl and —C(O)-(6 membered heteroaryl); wherein the aryl or heteroaryl group, whether alone or as part of a substituent group is optionally substituted with one or more substituents independently selected from halogen, hydroxy, $C_{1-4}$alkyl, $C_{1-4}$alkoxy, cyano, nitro or $CF_3$;
provided that when $R^1$ is hydrogen or halogen, $R^2$ is hydrogen, a is 0 and $R^3$ is 4-hydroxy-phenyl, then $R^4$ is other than 4-chlorophenyl;
provided further that when $R^1$ is halogen, $R^2$ is hydrogen, a is 1, $L^1$ is —C(O)NH— and $R^3$ is phenyl, then $R^4$ is other than hydrogen;
or a pharmaceutically acceptable salt thereof.

2. A compound as in claim 1, wherein
$R^1$ is selected from the group consisting of hydrogen, halogen, cyano, $CF_3$ and —O—$SO_2$—$CF_3$;
$R^2$ is selected from the group consisting of hydrogen, halogen, cyano, $CF_3$ and —O—$SO_2$—$CF_3$;
provided that $R^1$ and $R^2$ are not each hydrogen;
a is an integer from 0 to 1;
$L^1$ is selected from the group consisting of —C(O)—, —CH(OH)— and —C(O)—$NR^A$—; wherein $R^A$ is selected from hydrogen or $C_{1-4}$alkyl;
$R^3$ is selected from the group consisting of hydrogen, $C_{1-4}$alkyl and aryl;
wherein the aryl is optionally substituted with one or more independently selected from halogen, hydroxy, $C_{1-4}$alkyl, $C_{1-4}$alkoxy, cyano, nitro or $CF_3$;

alternatively, L$^1$-R$^3$ is methoxy methyl or 2-(Trimethylsilyl)ethoxy methyl;

provided that when a is 0, then R$^3$ is other than hydrogen or C$_{1-4}$alkyl;

provided further that when a is 1 and L$^1$ is —CH(OH)—, then R$^3$ is other than hydrogen;

R$^4$ is selected from the group consisting of hydrogen, —CH=CH—, aryl and —C(O)-aryl; wherein the aryl, whether alone or as part of a substituent group, is optionally substituted with one or more independently selected from halogen, hydroxy, C$_{1-4}$alkyl, C$_{1-4}$alkoxy, cyano, nitro or CF$_3$;

provided that when R$^1$ is hydrogen or halogen, R$^2$ is hydrogen, a is 0 and R$^3$ is 4-hydroxy-phenyl, then R$^4$ is other than 4-chlorophenyl;

provided further that when R$^1$ is halogen, R$^2$ is hydrogen, a is 1, L$^1$ is —C(O)NH— and R$^3$ is phenyl, then R$^4$ is other than hydrogen;

or a pharmaceutically acceptable salt thereof.

3. A compound as in claim 2, wherein

R$^1$ is selected from the group consisting of halogen, cyano and —O—SO$_2$—CF$_3$;

R$^2$ is selected from the group consisting of hydrogen, cyano and —O—SO$_2$—CF$_3$;

a is an integer from 0 to 1;

L$^1$ is selected from the group consisting of —C(O)—, —CH(OH)— and —C(O)—NR$^A$—; wherein R$^A$ is selected from hydrogen, methyl or ethyl;

R$^3$ is selected from the group consisting of hydrogen, C$_{1-4}$alkyl, —CH=CH—, and aryl; wherein the aryl is optionally substituted with one or more independently selected from halogen;

alternatively, L$^1$-R$^3$ is methoxy methyl;

provided that when a is 0, then R$^3$ is other than hydrogen or C$_{1-4}$alkyl;

provided further that when a is 1 and L$^1$ is —CH(OH)—, then R$^3$ is other than hydrogen;

R$^4$ is selected from the group consisting of hydrogen, aryl and —C(O)-aryl; wherein the aryl is optionally substituted with one to two substituents independently selected from hydroxy, halogen, C$_{1-4}$alkoxy or cyano;

provided that when R$^1$ is halogen, R$^2$ is hydrogen, a is 1, L$^1$ is —C(O)NH— and R$^3$ is phenyl, then R$^4$ is other than hydrogen;

or a pharmaceutically acceptable salt thereof.

4. A compound as in claim 3, wherein

R$^1$ is selected from the group consisting of fluoro, cyano and —O—SO$_2$—CF$_3$;

R$^2$ is selected from the group consisting of hydrogen, cyano and —O—SO$_2$—CF$_3$;

a is an integer from 0 to 1;

L$^1$ is selected from the group consisting of —C(O)—, —CH(OH)— and —C(O)—NH—;

R$^3$ is selected from the group consisting of hydrogen, methyl, —CH=CH—, 2-chlorophenyl, 3-chlorophenyl, 4-chlorophenyl, 2,3-dichlorophenyl, 2,4,-dichlorophenyl, 2,4,6-trichlorophenyl, 2-fluorophenyl and 2,4-difluorophenyl;

alternatively, L$^1$-R$^3$ is methoxy methyl provided that when a is 0, then R$^3$ is other than hydrogen or methyl;

provided further that when a is 1 and L$^1$ is —CH(OH)—, then R$^3$ is other than hydrogen;

R$^4$ is selected from the group consisting of hydrogen, 2,4-dihydroxyphenyl, 2,4-dimethoxyphenyl, 2-hydroxy-4-cyano-phenyl and 4-chlorophenyl-carbonyl-; or a pharmaceutically acceptable salt thereof.

5. A compound as in claim 4 selected from the group consisting of trifluoro-methanesulfonic acid 3-(2,4-dimethoxy-phenyl)-4-(2-methoxy-ethyl)-2-oxo-2H-chromen-7-yl ester; 3-(2,4-dihydroxy-phenyl)-2-oxo-4-vinyl-2H-chromene-7-carbonitrile; trifluoro-methanesulfonic acid 4-[2-(2,4-dichloro-phenyl)-2-hydroxy-ethyl]-2-oxo-2H-chromen-7-yl ester; trifluoro-methanesulfonic acid 2-oxo-4-[(2,4,6-trichloro-phenylcarbamoyl)-methyl]-2H-chromen-7-yl ester; 2-(7-cyano-2-oxo-2H-chromen-4-yl)-N-(2-fluoro-phenyl)-acetamide; N-(3-chloro-phenyl)-2-(7-cyano-2-oxo-2H-chromen-4-yl)-acetamide;

or a pharmaceutically acceptable salt thereof.

6. A pharmaceutical composition comprising a pharmaceutically acceptable carrier and a compound of claim 1.

7. A pharmaceutical composition made by mixing a compound of claim 1 and a pharmaceutically acceptable carrier.

* * * * *